United States Patent [19]

Green et al.

[11] Patent Number: 4,672,143
[45] Date of Patent: Jun. 9, 1987

[54] FLAME REACTOR FOR CRACKING HYDROCARBONS

[75] Inventors: Gary J. Green, Yardley; Tsoung-Y Yan, Philadelphia, both of Pa.

[73] Assignee: Mobil Oil Corporation, New York, N.Y.

[21] Appl. No.: 796,382

[22] Filed: Nov. 8, 1985

[51] Int. Cl.[4] ............................................... C07C 2/78
[52] U.S. Cl. ..................................... 585/540; 208/106; 585/403; 585/503; 585/505; 585/537; 585/539; 585/615; 585/636; 585/652; 585/943
[58] Field of Search ............... 585/403, 503, 505, 537, 585/539, 540, 615, 636, 652, 943; 208/106, 132

[56] References Cited

U.S. PATENT DOCUMENTS

| | | | |
|---|---|---|---|
| 3,153,104 | 10/1964 | Sprauer | 585/540 |
| 3,399,245 | 8/1968 | Knapp | 585/540 |
| 3,453,084 | 7/1969 | Ivernel et al. | 585/540 |
| 3,541,179 | 11/1970 | Okagami et al. | 585/540 |
| 4,136,015 | 1/1979 | Kamm et al. | 208/129 |

FOREIGN PATENT DOCUMENTS

908351  10/1962  United Kingdom ............... 208/106

Primary Examiner—Asok Pal
Attorney, Agent, or Firm—Alexander J. McKillop; Michael G. Gilman; Charles J. Speciale

[57] ABSTRACT

A diffusion flame reactor for cracking hydrocarbon gas has an oxygen-deficient zone in the center of the flame or in the center of an array of flames. Propane, n-octane, iso-octane and decalin are cracked to ethylene, acetylene, propylene, butenes, and butadienes which are withdrawn from the flame.

9 Claims, 9 Drawing Figures

FLAME REACTOR FOR CRACKING HYDROCARBONS

BACKGROUND OF THE INVENTION

The present invention relates to the cracking of hydrocarbons and more particularly to a diffusion flame reactor for hydrocarbon gas.

Cracking is extensively used in petroleum processing for fracturing hydrocarbon molecules into smaller fragments. Thermal cracking, including catalytic cracking and hydrocracking, are extensively used for converting residual crude fractions or a heavy distillate into gasoline and light distillates, or reducing the viscosity of residual fractions, or for the production of coke. Coking and visbreaking are extensively used to convert hydrocarbons into more valuable products.

In particular, the manufacture of ethylene, acetylene, propylene, butenes, and butadienes from hydrocarbons having carbon number from 2 to 10 is an important part of petroleum processing.

It is an object of the present invention to crack hydrocarbons with a flame reactor which has no walls around the reaction zone.

It is another object of the present invention to minimize the problems of heat transfer across reactor walls and wall coking.

It is another object of the present invention to improve the efficiency of the cracking process.

RELATED APPLICATIONS

"FLAME CONVERSION OF METHANE TO MORE REACTIVE HYDROCARBONS", Green, Ser. No. 796,366, filed 11/08/85 describes a single flame burner. That application is incorporated by reference herein.

SUMMARY OF THE INVENTION

Hydrocarbons are cracked, by pyrolysis in the center of a diffusion flame, or flame array, which has an interior which is at high temperature and is oxygen-deficient. In accordance with the invention, the interior of such a flame forms a reactor for cracking the hydrocarbons. Such a reactor is embodied by a diffusion flame, as in the aforementioned Green application, or it is a flame array in a cylindrical or tubular configuration with a high temperature, oxygen-deficient zone at the center of the configuration.

In accordance with the invention, light hydrocarbons, primarily $C_2$–$C_4$'s and naphtha, are cracked to valuable products such as ethylene, acetylene, propylene, butenes, and butadienes. The flame or flame array is preferably in a cylindrical or tubular configuration oriented in the vertical direction. Fuel for the flame may be a portion of the feed stream itself or another hydrocarbon fuel which may be more readily available or less expensive. The feed is passed into the interior of the flame zone which is at high temperature and is oxygen-deficient. The flow rate of the feed is adjusted to optimize the residence time for good conversion and selectivity to the desired products.

Products are quenched/collected as they exit the flame zone with any unreacted feed. This unreacted feed is then recycled to the flame reactor. Since there are no walls associated with the reaction zone itself, problems with limited heat transfer across reactor walls and wall coking are eliminated. Therefore, the overall efficiency of the cracking process is improved using this scheme.

DESCRIPTION OF THE PREFERRED EMBODIMENT

Figure 1:
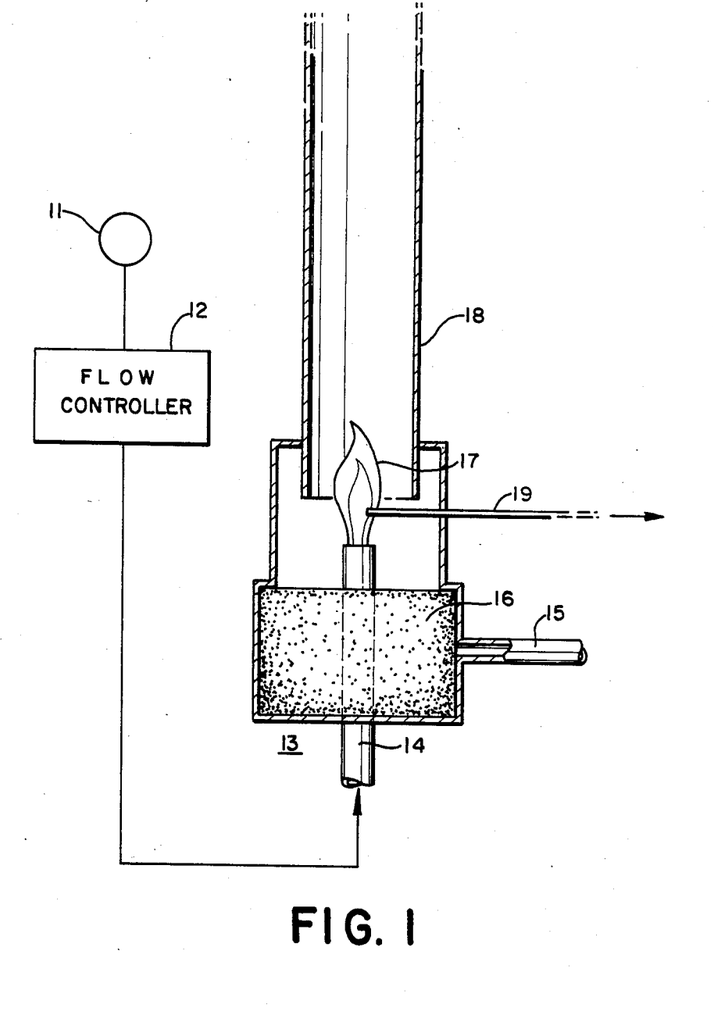
FIG. 1 depicts cracking in a single diffusion flame.

In FIG. 1, hydrocarbons from a source 11 are fed through flow controller 12 to the diffusion flame burner 13 which includes burner tube 14, with the hydrocarbon gas being supplied to the bottom of the tube. Oxidizing gas flows past the top of burner tube 14. In an exemplary embodiment, a 40% $O_2$/60% $N_2$ mixture was fed to the inlet 15. The oxidizing gas flows through the coarse steel wool 16 upwardly past the top end of burner tube 14.

A diffusion flame 17 is produced at the top of burner tube 14. A chimney 18 carries away soot and other combustion products. Cracked products are withdrawn from the center of the flame by the probe tube 19. The products are cooled convectively by the flowing oxidizing gas stream around the flame. This rapidly quenches the more cracked products, thereby stopping the reaction as desired.

As used herein, "diffusion flame" may be a single flame wherein hydrocarbons without oxidizing gas mixed therein are burned in a flame with oxidizing air being supplied to the outside of the flame. The reaction in the center of the flame is complex. Basically, it is pyrolisis wherein hydrogen atoms are stripped from the hydrocarbon gas.

For example, acetylene, $C_2H_2$; ethylene, $C_2H_4$; and ethane $C_2H_6$ are produced. More complex propylene and butadiene are produced, depending on the residence time in the flame.

The present invention provides a simple way to crack hydrocarbon gas to $C_2+$ materials which are valuable petrochemical feedstocks.

The cracking levels can be maximized by recycling to the flame any unreacted gas which is collected, making the process multi-pass.

Figure 2A:
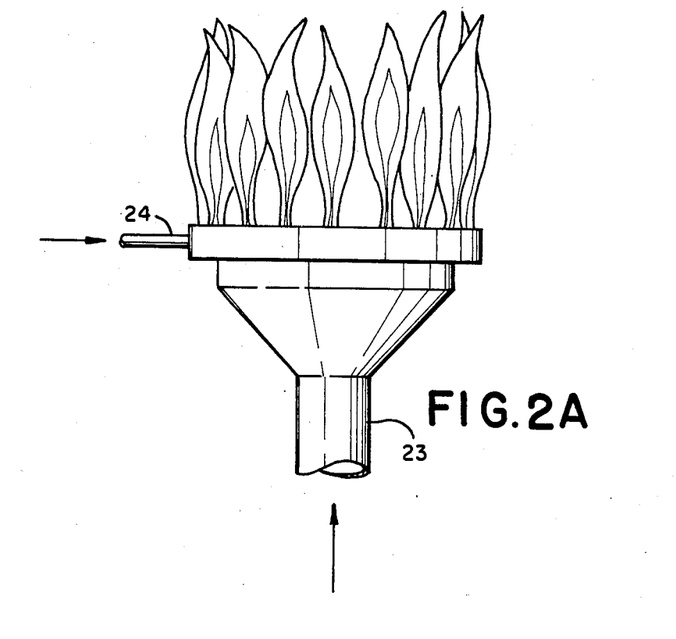
FIG. 2A is a side view of a flame ring reactor.
Figure 2B:
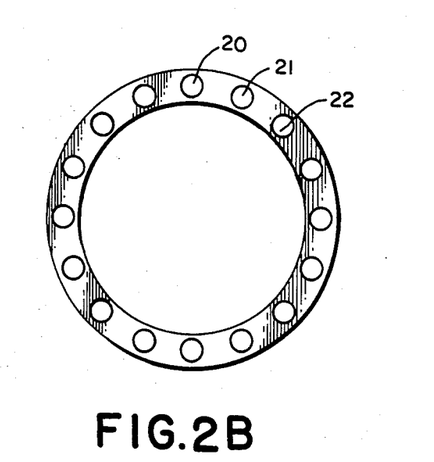
FIG. 2B is a top view of the reactor of FIG. 2A.

As used herein, the term "diffusion flame" may be a single flame as shown in FIG. 1, or it may be an array of flames with an oxygen-deficient zone in the center thereof, as shown in FIGS. 2A–2B. A circular array of fuel gas jets 20, 21, 22 and others establish a flame ring, or tubular flame, which is oriented in a vertical direction. The flames may be pre-mixed with air or other oxidant, or they may be pure fuel with the oxygen supplied from the outside of the flame array.

The fuel for the flames is fed to the inlet 23 of the reactor and the feed gas is fed to the inlet 24. The fuel feed for the flames may be the same, or different, than the gas supplied to the reactor feed inlet 24.

The gas jets 20-22 are closely spaced and form flames which are the reactor walls, as well as the heat source. This flame is operated at stoichiometric, or slightly fuel-rich, to ensure minimal oxygen content in the interior of the flame ring. The feed gas flows into the interior of the flame ring, along the central vertical axis where it undergoes pyrolysis to generate cracked products.

The diameter of the flame ring, as well as its vertical dimension, are determined by the specific feed or feed/fuel combination to the burner such that the feed residence time/temperature history is optimized for product selectivity and conversion.

Figure 2C:
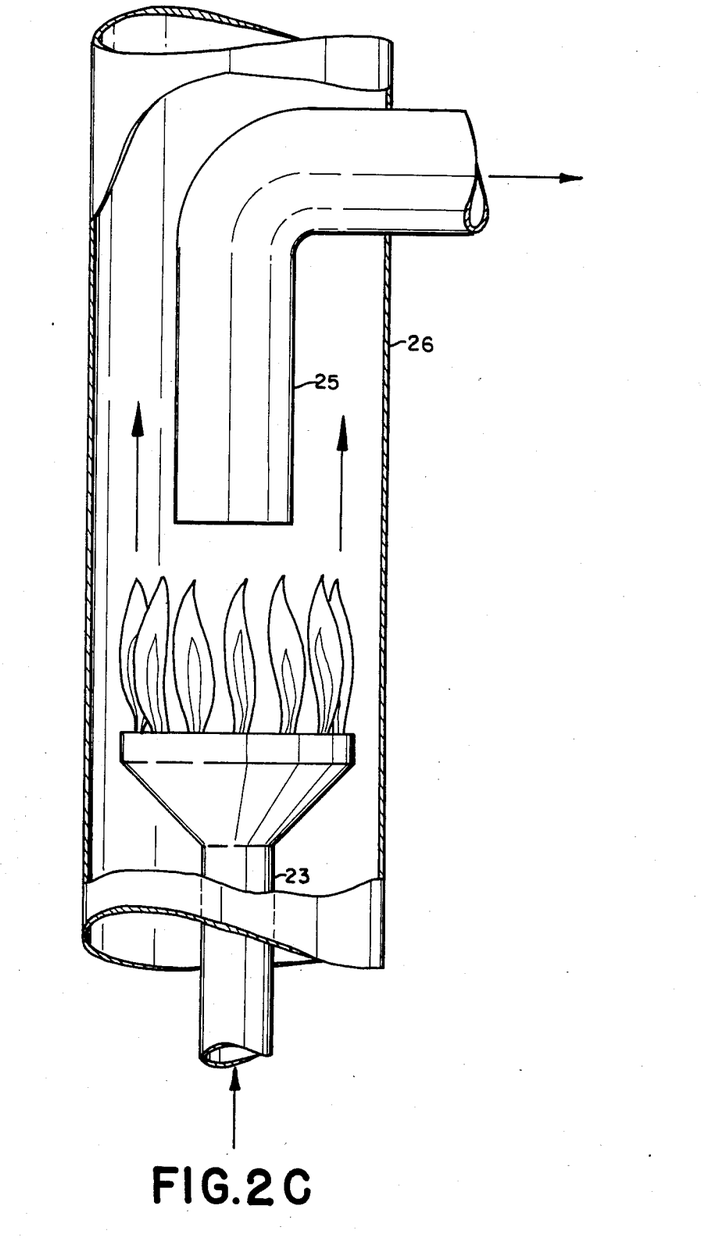
FIG. 2C shows a flame ring reactor with the collector.

The product stream is collected as it exits from the top of the flame ring by means of a sampling cap 25, as shown in FIG. 2C. The flame ring reactor is enclosed within the walls of a furnace 26 which exhausts the $CO_2$, $H_2O$ combustions products from the flames.

Another embodiment of the flame ring reactor is one in which the circular array of fuel jets is replaced by a thin slot which encircles the burner.

Figure 2D:
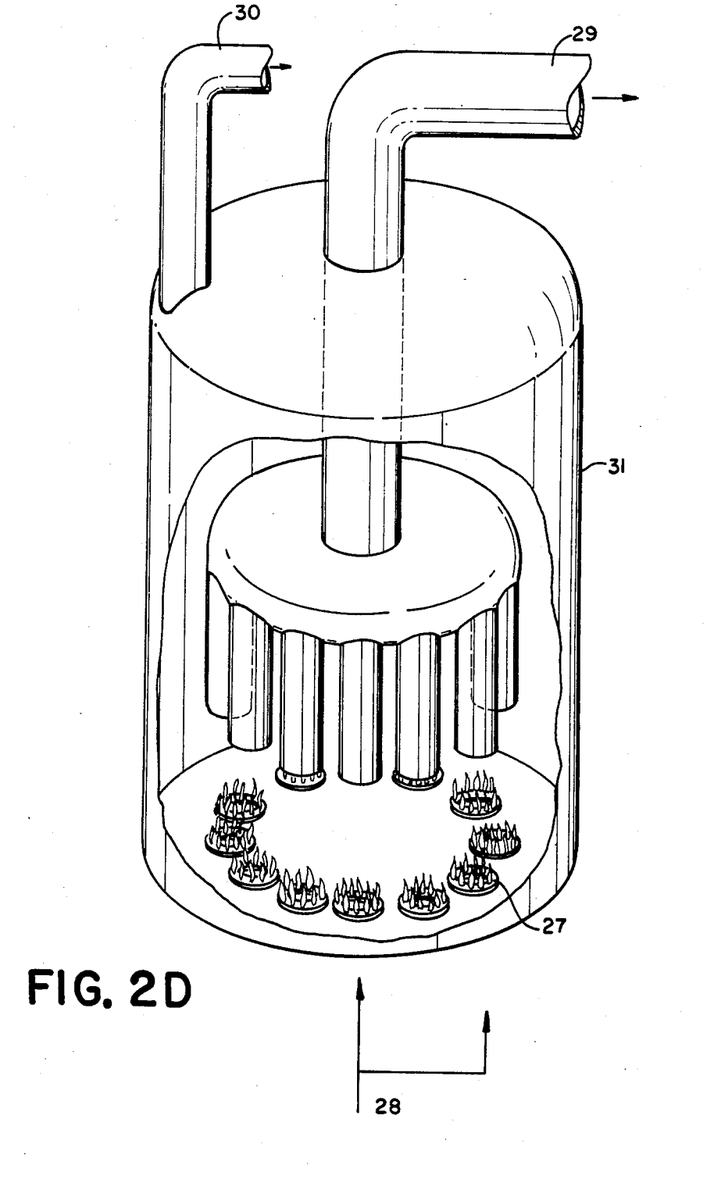
FIG. 2D shows a flame ring reactor bank and collectors.

If an optimum flame ring dimension is realized for a given feed, but restricts the total throughput below that desired, a bank 27 of these flame ring reactors can be assembled as shown in FIG. 2D. Each is connected to a common feed line 28, and each of the collection caps is connected a common product withdrawal line 29. Products of combustion, primarily $CO_2$ and $H_2O$, are collected separately via a single, overhead take-off port 30. The bank of flame ring reactors is enclosed in a refractory-line steel structure 31, the interior atmosphere of which is always oxygen-deficient due to operating the flame bank at stoichiometric or slightly fuel-rich.

The present invention can be used in a cracking process for light olefin manufacture with improved thermal efficiency. For a large volume chemical feedstock such as ethylene, small gains in efficiency would result in large savings in manufacturing costs. Since the reactor operates without walls, high temperature materials limitations such as coking, corrosion and heat transfer are eliminated, leading to a process concept which is particularly useful for production of acetylene and butadiene.

EXAMPLES

The following examples were performed with the laminar diffusion flame burner shown in FIG. 1.

Hydrocarbons were precisely metered to the burner via a mass flow controller while a 40% $O_2/N_2$ mixture was supplied separately to the burner at a flow rate of 12.5 liters/min. The products were withdrawn from the flame using either a stainless steel or quartz capillary sampling probe, collecting at a rate of approximately 5 cc/min. The reaction products were rapidly quenched by the withdrawal through the sampling probe which is cooled convectively by the flowing $O_2/N_2$ gas stream around the flame.

Figure 3:
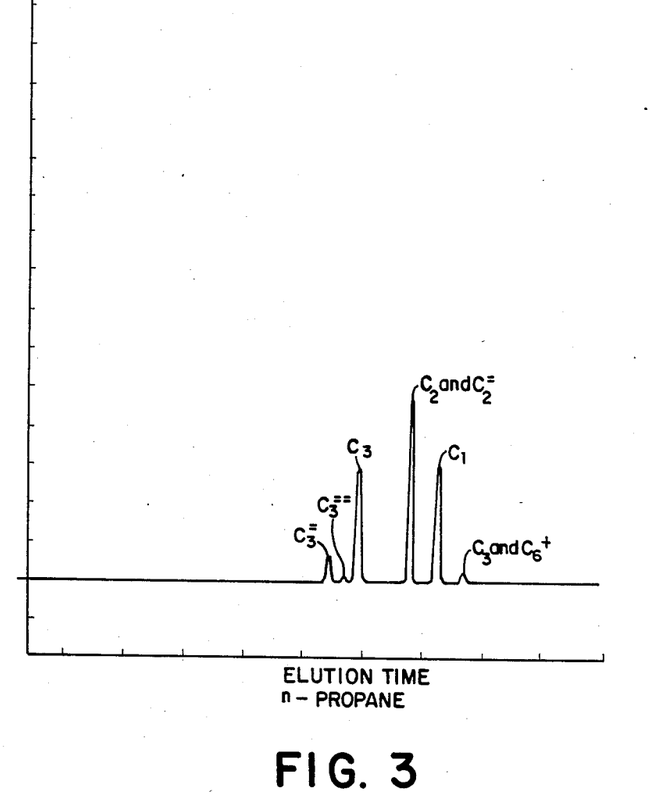
FIG. 3 shows a chromatogram of products withdrawn from an n-propane flame reaction.

FIG. 3 shows a gas chromatogram of the gases sampled from an n-propane diffusion flame burning as described above. These gases were collected at a point corresponding to a residence time of approximately 200 m/sec. An analysis of the hydrocarbons shows the presence of ethane, ethylene, and acetylene, and other cracked products.

Figure 4:
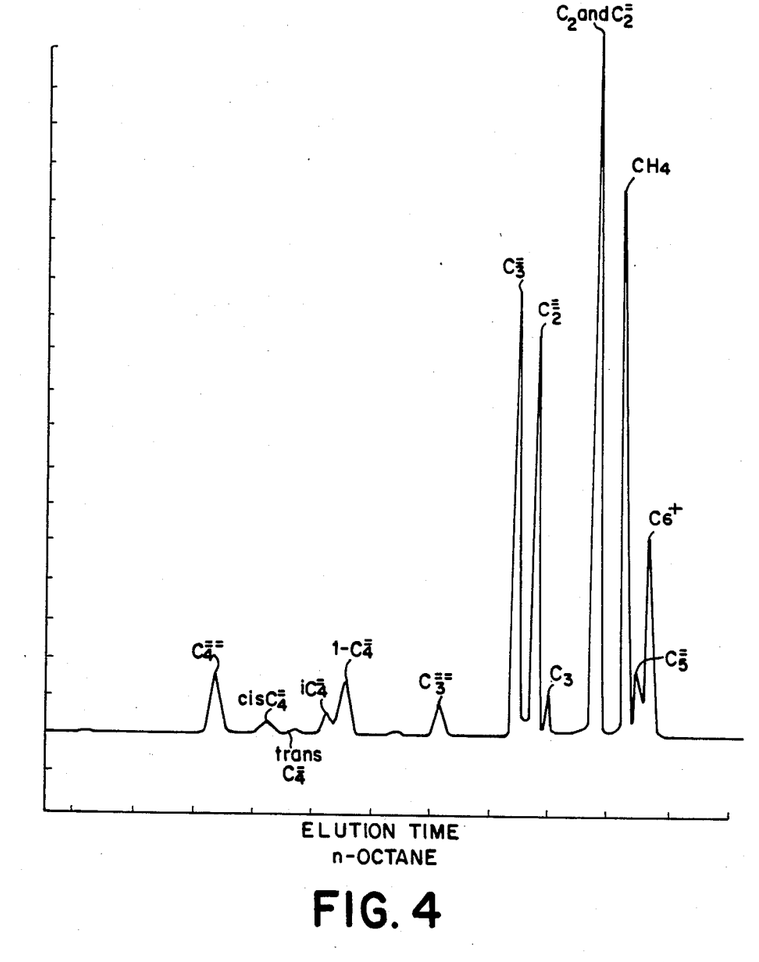
FIG. 4 shows a chromatogram of products withdrawn from an n-octane flame reaction.
Figure 5:
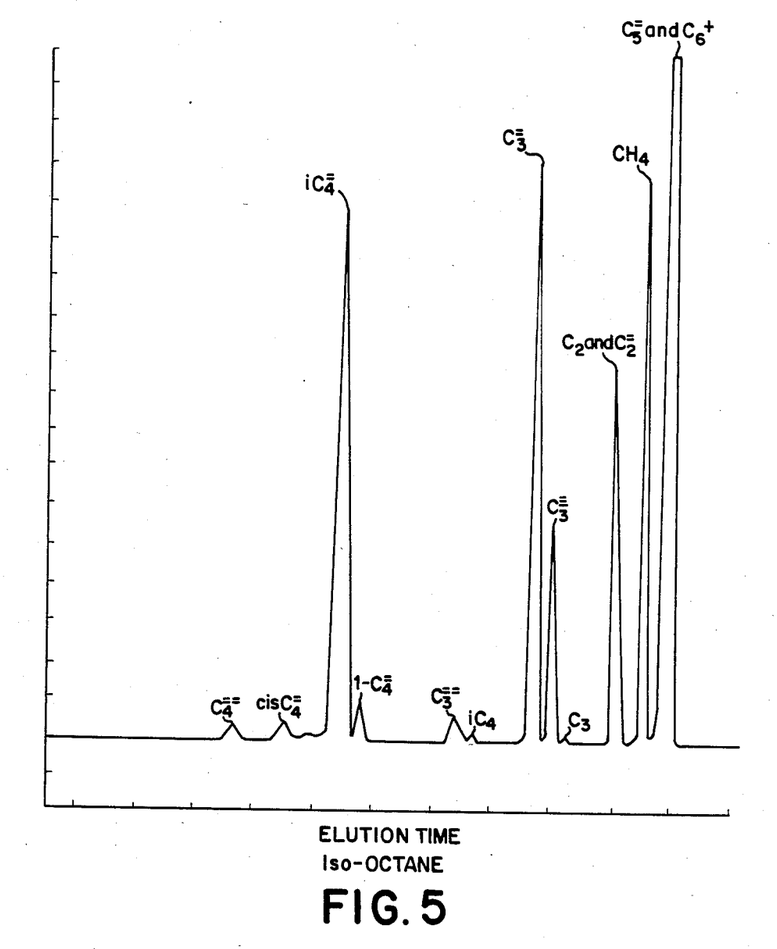
FIG. 5 shows a gas chromatogram of products withdrawn from an iso-octane flame.
Figure 6:
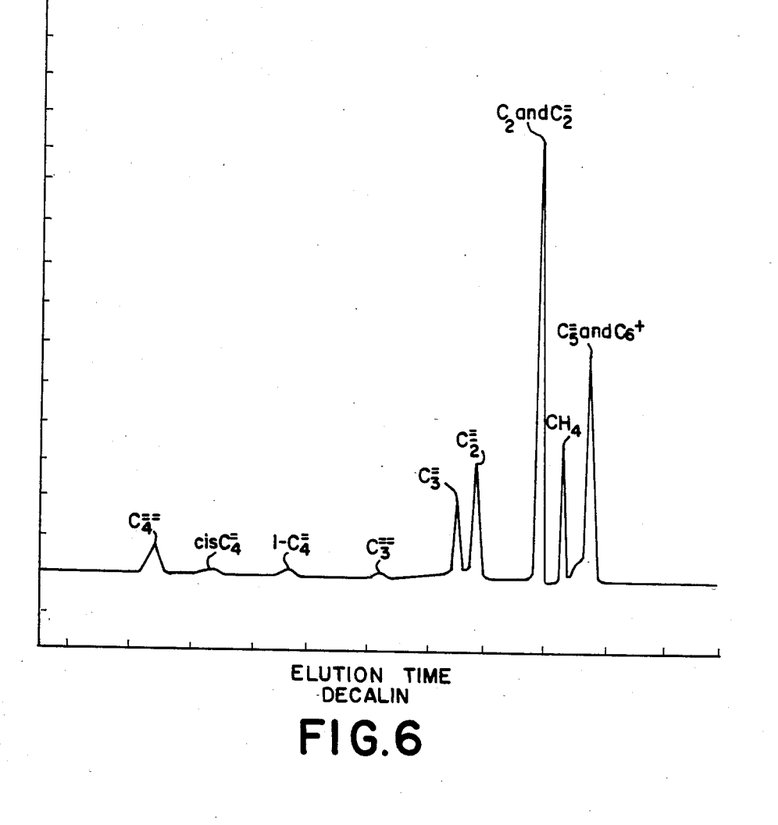
FIG. 6 shows a gas chromatogram of products withdrawn from a decalin flame reaction.

FIGS. 4, 5 and 6 show gas chromatograms of sampled product gases from n-octane, iso-octane, and decalin diffusion flames, demonstrating the applicability of the concept to higher carbon number, saturated materials. Among the major products are unsaturates such as ethylene, acetylene, propylene, butylene and butadiene. By controlling the residence time in the flame, and the flow rate, the type of reaction product can be controlled. Examples of this are shown in the aforementioned Green application.

FIGS. 3-6 were produced by a Carle refinery gas analyzer.

While a particular embodiment of the invention has been shown and described, various modifications are within the true spirit and scope of the invention. The appended claims are, therefore, intended to cover all such modifications.

We claim:

1. The method of cracking hydrocarbons comprising:
   heating hydrocarbons in the oxygen-deficient center of a diffusion flame;
   pyrolyzing the hydrocarbons to be cracked by pyrolysis in said oxygen-deficient center of said diffusion flame; and
   withdrawing the cracked products from said oxygen-deficient center of said diffusion flame without mixing with the combustion products.

2. The method recited in claim 1 further comprising: flowing oxidizing gas outside of said diffusion flame.

3. The method recited in claim 2 further comprising: cooling the withdrawn products to stop the reaction after withdrawal.

4. The method recited in claim 3 wherein the step of cooling is carried out by passing the withdrawn gas through the flowing oxidizing gas.

5. The method recited in claim 1 wherein said hydrocarbons are from the group consisting of propane, n-octane, iso-octane, and decalin.

6. The method recited in claim 1 wherein said cracked products have carbon numbers from 2 to 10.

7. The method recited in claim 6 wherein said cracked products are from the group consisting of ethylene, acetylene, propylene, butenes and butadiene.

8. The method recited in claim 1 further comprising:
   controlling the residence time of said gas in the center of said flame to control the type of cracked products which are produced.

9. The method recited in claim 2 wherein said oxidizing gas is a mixture of oxygen and nitrogen.

* * * * *